(12) United States Patent
Huang et al.

(10) Patent No.: US 8,998,679 B2
(45) Date of Patent: *Apr. 7, 2015

(54) SURFACE TREATMENT OF A POLYMERIC STENT

(71) Applicant: Abbott Cardiovascular Systems Inc., Santa Clara, CA (US)

(72) Inventors: Bin Huang, Pleasanton, CA (US); David C. Gale, Kennesaw, GA (US); Daniel Castro, Mountain View, CA (US); Timothy A. Limon, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/280,471

(22) Filed: May 16, 2014

(65) Prior Publication Data

US 2014/0252683 A1 Sep. 11, 2014

Related U.S. Application Data

(62) Division of application No. 12/902,082, filed on Oct. 11, 2010, now Pat. No. 8,795,030, which is a division of application No. 11/453,175, filed on Jun. 13, 2006, now abandoned.

(51) Int. Cl.
*A61F 2/07* (2013.01)
*A61F 2/82* (2013.01)
*C08J 7/02* (2006.01)
*A61F 2/91* (2013.01)

(52) U.S. Cl.
CPC ... *A61F 2/82* (2013.01); *A61F 2/91* (2013.01); *A61L 2400/18* (2013.01); *C08J 7/02* (2013.01)

(58) Field of Classification Search
USPC ......... 451/36, 38, 54, 57, 60, 65, 69, 70, 104, 451/113; 623/1.15, 1.42; 427/2.24, 2.25, 427/2.28, 2.3, 335; 604/9
See application file for complete search history.

(56) References Cited

U.S. PATENT DOCUMENTS

| | | | | |
|---|---|---|---|---|
| 3,787,239 | A * | 1/1974 | Schroeder et al. | 134/2 |
| 5,298,276 | A * | 3/1994 | Jayaraman | 427/2.25 |
| 5,788,558 | A * | 8/1998 | Klein | 451/36 |
| 5,906,759 | A * | 5/1999 | Richter | 219/121.63 |
| 5,939,136 | A * | 8/1999 | Cronk et al. | 427/163.2 |
| 6,086,455 | A * | 7/2000 | Frantzen | 451/36 |
| 6,120,847 | A * | 9/2000 | Yang et al. | 427/335 |
| 6,322,847 | B1 * | 11/2001 | Zhong et al. | 427/2.28 |
| 6,375,826 | B1 * | 4/2002 | Wang et al. | 205/684 |
| 6,492,615 | B1 * | 12/2002 | Flanagan | 219/121.66 |
| 6,679,980 | B1 * | 1/2004 | Andreacchi | 204/272 |
| 6,761,784 | B1 * | 7/2004 | Hage | 156/155 |
| 7,101,259 | B2 * | 9/2006 | Kimura et al. | 451/8 |
| 7,122,125 | B2 * | 10/2006 | Deshmukh et al. | 216/63 |
| 7,312,160 | B2 * | 12/2007 | Aoki et al. | 438/748 |
| 7,329,366 | B1 * | 2/2008 | Gale et al. | 216/88 |
| 7,462,175 | B2 * | 12/2008 | Chang et al. | 604/510 |
| 7,556,837 | B2 * | 7/2009 | Hossainy | 427/2.24 |

(Continued)

FOREIGN PATENT DOCUMENTS

EP 1779817 A1 * 5/2007 ............... A61F 2/82

*Primary Examiner* — Eileen P. Morgan
(74) *Attorney, Agent, or Firm* — Squire Patton Boggs (US) LLP

(57) ABSTRACT

Methods of treating the polymeric surfaces of a stent with a fluid including a solvent for the surface polymer are disclosed.

16 Claims, 7 Drawing Sheets

(56) References Cited

U.S. PATENT DOCUMENTS

| | | | |
|---|---|---|---|
| 8,252,361 B2* | 8/2012 | Kramer-Brown et al. | 427/2.1 |
| 2004/0224528 A1* | 11/2004 | Mirth | 438/759 |
| 2004/0249437 A1* | 12/2004 | Sundar | 623/1.15 |
| 2006/0079095 A1* | 4/2006 | McReynolds et al. | 438/725 |
| 2006/0193887 A1* | 8/2006 | Owens et al. | 424/423 |
| 2007/0110889 A1* | 5/2007 | Sundar | 427/2.3 |
| 2007/0208413 A1* | 9/2007 | Nakano | 623/1.15 |
| 2010/0109204 A1* | 5/2010 | Wu | 264/446 |

* cited by examiner

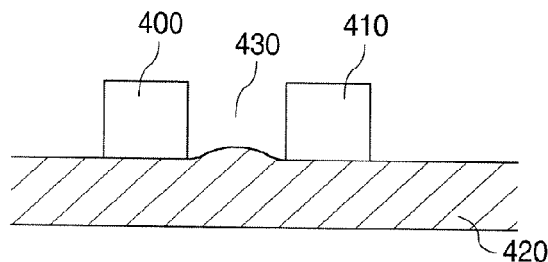
FIG. 4A
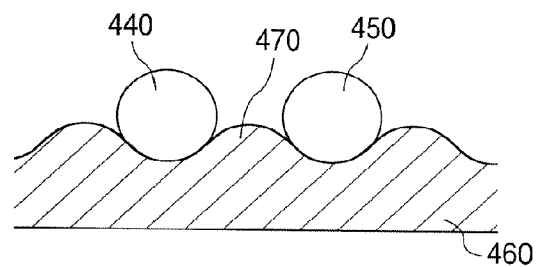
FIG. 4B
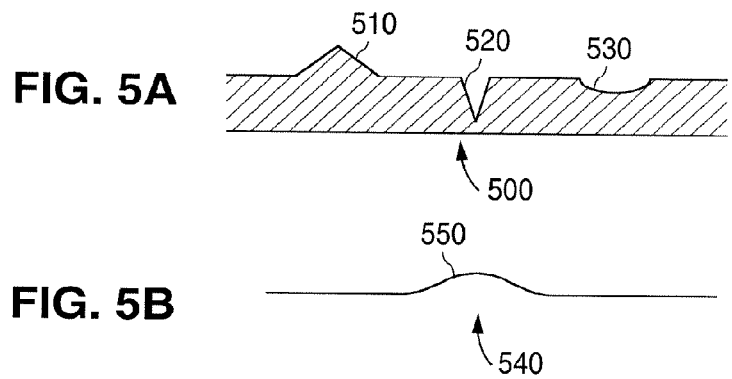
FIG. 5A
FIG. 5B
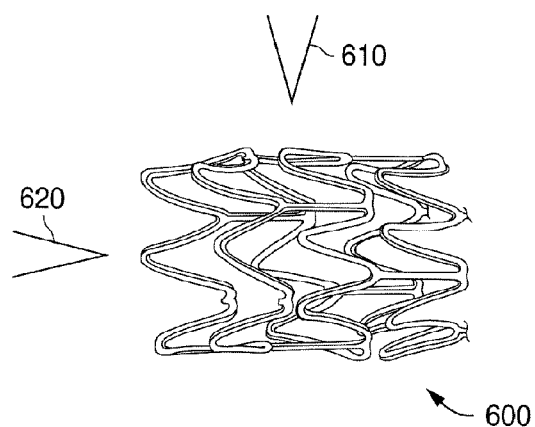
FIG. 6

SURFACE TREATMENT OF A POLYMERIC STENT

CROSS REFERENCE

This is a divisional of application Ser. No. 12/902,082, filed Oct. 11, 2010, which is a divisional of application Ser. No. 11/453,175, filed Jun. 13, 2006.

BACKGROUND OF THE INVENTION

1. Field of the Invention

This invention relates to methods of treating surfaces of polymeric stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

The biocompatibility of a stent is extremely important for successful treatment of a bodily lumen. The surface finish and surface profile of a stent are important factors for biocompatibility. Polymeric stents or stent having polymeric surface can have surface imperfections, such as cracks and pits, or a sharp edges that can cause or increase the likelihood of thrombosis or inflammatory reactions due to turbulence in blood flow around a sharp edge. Additionally, some surface features can cause mechanical instability. For a coating, such imperfections can be the result of the coating process. Imperfections and sharp edges can be remnants of laser machining Therefore, methods to reduce or eliminate surface imperfections and sharp profiles are desirable.

SUMMARY OF THE INVENTION

Certain embodiments of the present invention are directed to a method for treating a polymeric surface of a stent comprising: contacting a polymeric surface of a stent with a first fluid, the first fluid comprising a solvent for the surface polymer, the solvent capable of dissolving the surface polymer; allowing the solvent to modify at least a portion of the polymeric surface by dissolving at least a portion of the surface polymer; and contacting the polymeric surface with a second fluid miscible with the solvent to remove all or a majority of the first fluid from the polymeric surface, the second fluid comprising a non-solvent for the surface polymer.

Further embodiments of the present invention are directed to a method for treating a polymeric surface of a stent comprising contacting a polymeric surface of a stent with a gas stream, the gas stream comprising a solvent for the surface polymer, the solvent capable of dissolving the surface polymer, wherein the solvent in the gas is allowed to modify at least a portion of the polymeric surface by dissolving at least a portion of the surface polymer. Further embodiments of the present invention are directed to a method for treating a polymeric surface of a stent comprising: contacting a polymeric surface of a stent with a fluid mixed with particles, the first fluid comprising a solvent for the surface polymer, the solvent capable of dissolving the surface polymer; and allowing the solvent in the fluid and the particles to modify at least a portion of the polymeric surface, the solvent modifying the surface by dissolving at least a portion of the surface polymer, the particles modifying the surface by abrading the polymeric surface.

BRIEF DESCRIPTION OF THE DRAWINGS

FIG. 4A depicts struts having square cross-sections from a stent crimped onto a balloon.

FIG. 4B depicts rounded struts from a stent crimped onto a balloon.

FIG. 5A-B depicts imperfections on a stent surface.

FIG. 6 depicts a stent with a nozzle positioned above a stent and a nozzle directed into a proximal end of the stent.

DETAILED DESCRIPTION OF THE INVENTION

The various embodiments of the present invention relate to methods of treating a polymeric surface of a stent with a treatment fluid to increase the biocompatibility of a stent. In several embodiments, the polymeric surface is treated to remove sharp edges and reduce or eliminate surface imperfections. The polymeric surface may refer to a surface of a polymeric substrate, scaffolding, or body of a stent. Additionally, a polymeric surface may refer to a surface of a polymer coating disposed over a substrate, scaffolding, or body composed of metal, polymer, ceramic, or other suitable material.

The present invention may be applied to devices including, but not limited to, self-expandable stents, balloon-expandable stents, stent-grafts, and grafts (e.g., aortic grafts). A stent can have a scaffolding or a substrate that includes a pattern of a plurality of interconnecting structural elements or struts.

Figure 1:
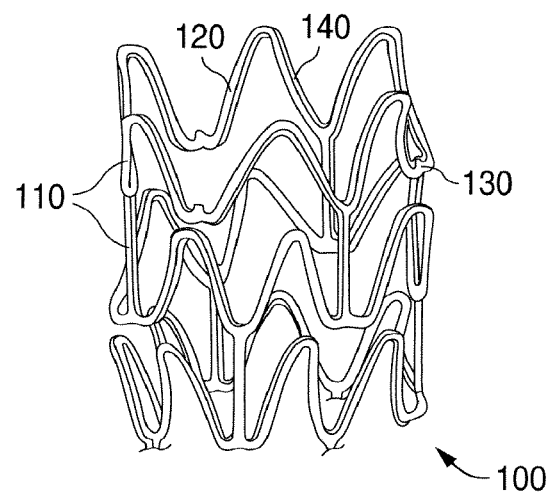
FIG. 1 depicts a stent.

FIG. 1 depicts an example of a view of a stent 100. Stent 100 has a pattern that includes a number of interconnecting elements or struts 110. The embodiments disclosed herein are not limited to stents or to the stent pattern illustrated in FIG. 1. The embodiments are easily applicable to other patterns and other devices. The variations in the structure of patterns are virtually unlimited. Struts 110 of stent 100 include luminal faces or surfaces 120, abluminal faces or surfaces 130, and side-wall faces or surfaces 140. Stent 100 may be fabricated by laser cutting a pattern on a tube or a sheet rolled into a tube. Representative examples of lasers that may be used include, but are not limited to, excimer, carbon dioxide, and YAG. In other embodiments, chemical etching may be used to form a pattern on a tube.

Figure 2:
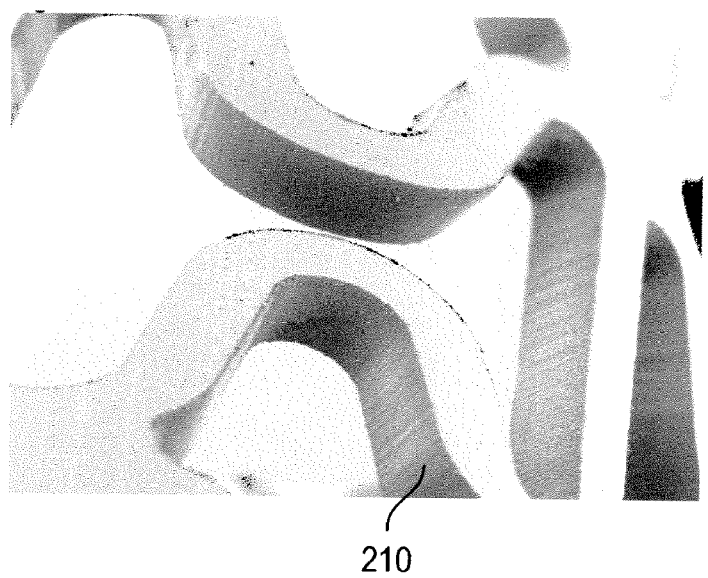
FIG. 2 depicts an image of a stent strut formed by laser cutting a poly(L-lactide) tube.

A stent strut of a polymeric substrate formed by laser cutting tends to have relatively sharp edges. The sharp edges are illustrated in FIG. 2 which depicts an image of a stent strut formed by laser cutting a poly(L-lactide) tube. Surface 210 corresponds to a cut surface or sidewall surface. Due to the heat of the laser, low molecular weight material is deposited on the cut surface. Also, since polymers tend to have lower strength than metals on a per unit mass basis, the thickness of struts of polymeric stents tend to be thicker than metallic stents. Laser cutting techniques can result in a heat affected zone on a substrate cut by a laser. A heat affected zone refers to a region of a target material affected, but not removed, by the heat of the laser. In particular, the heat from the laser can negatively impact mechanical properties of a substrate.

Figure 3A:
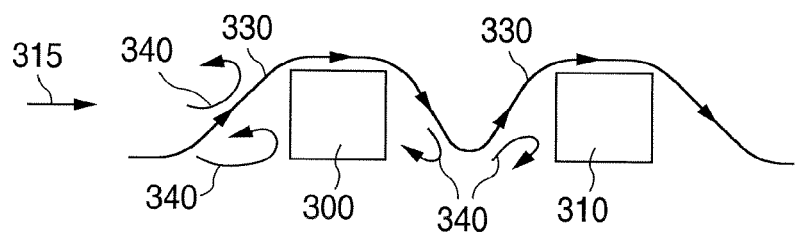
FIG. 3A illustrates blood flow past struts having sharp edges.
Figure 3B:
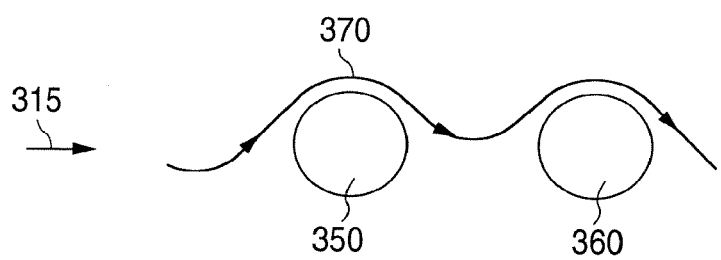
FIG. 3B illustrates blood flow past struts having rounded cross-sections.

The sharp edges and thicker struts can cause problems during use of a polymeric stent. The sharp edges can cause vessel injury during delivery, deployment, and after deployment. The thickness and sharp edges can result in blood flow turbulence. FIG. 3A illustrates blood flow past struts having sharp edges. FIG. 3A depicts axial cross-sections of struts 300 and 310 with square cross-sections with arrow 315 showing the direction of blood flow. Arrow 320 depicts the blood flow around and past struts 300 and 310. Turbulent flow can be present in regions adjacent to struts 300 and 310 as shown by arrows 340. FIG. 3B illustrates blood flow past struts having rounded cross-sections. Arrow 370 shows the flow of blood around rounded struts 350 and 360 which has less turbulence.

In addition, sharp edges and thicker struts can result in reduced retention of a crimped stent on a balloon. In general, stent retention is facilitated by penetration of balloon material into the gaps between stent struts. Since the stents are thicker and have sharp edges, the gaps are smaller resulting in less balloon material penetrating into the gaps. As an illustration, FIG. 4A depicts struts 400 and 410 having square cross-sections from a stent crimped onto a balloon 420. Balloon material is shown to penetrate into gap 430 between struts 400 and 410. FIG. 4B depicts rounded struts 440 and 450 from a stent crimped onto balloon 460. A greater amount of balloon material is shown to penetrate into gap 470 between struts 440 and 450. Additionally, a rounded profile may result in less stress on the struts during crimping.

Additionally, the polymer surface of a stent substrate or a coating often includes various types of imperfections or features that tend to make the stent more susceptible to thrombosis and/or mechanical instability. Such imperfections or features can activate fibrin and/or platelets to form thrombus. These imperfections can be formed as a by-product of coating and fabrication processes including extrusion, injection molding, and laser cutting. The imperfections may include cracks, pitting, and/or jagged edges. FIG. 5A depicts a surface 500 which is an expanded cross-section of a portion of a surface of stent 100 in FIG. 1. Surface 500 includes a jagged edge 510, a crack 520, and a pit 530.

The presence of such imperfections on the surface of a stent tends to facilitate the rapid formation of thrombus when implanted in a bodily lumen. It is believed that thrombus formation is facilitated by such imperfections. Without being bound by any particular theory, imperfections on a surface may serve as sites at which platelets may attach which may then lead to thrombus formation. Removing and/or reducing such imperfections may decrease the number of sites for attachment to a surface and/or reduce the tendency for platelets to attach to a surface, respectively, of a stent. Therefore, thrombus formation may be significantly reduced. Reducing an imperfection may refer to reducing the degree or size of an imperfection in a way that improves surface quality. For example, reducing an imperfection may correspond to smoothing a jagged edge. FIG. 5B depicts a surface 540 which is another expanded cross-section of a surface of stent 100 depicted in FIG. 1. Feature 550 is a smoothed edge that may result in significantly less platelet attachment than jagged edge 510 in FIG. 5A. As a result, the surface in FIG. 5A may result in significantly less thrombosis than the surface of FIG. 5B.

Furthermore, the presence of features such as cracks or pitting in a stent may cause mechanical instability in the stent. In general, some features, in particular cracks, tend to result in stress concentration localized at or near the imperfection. Such features may be referred to as "stress concentrators." Irregularities or discontinuities in the shape of an object can result in steep gradients of stress at or near the irregularity or discontinuity. Stress is concentrated at an irregularity or discontinuity because a load on an object cannot be uniformly distributed across the full area of the object. Therefore, the load must be redistributed across a missing cross-section of the object. Moreover, stress concentrators may lead to failure of a material since fracture always starts at some point of stress concentration. Failure and fracture mechanics of polymers and other types of materials are well known and are discussed in many publications, for example, "Deformation and Fracture Mechanics of Engineering Materials," Richard W. Hertzberg, 4th edition, John Wiley & Sons, December 1995. Since stents are subjected to stress both before and during treatment, it may be desirable to reduce or remove imperfections from its surface to increase mechanical stability of the stent.

Therefore, it is advantageous to treat the surface of a stent to round sharp edges and to reduce or remove imperfections.

Some embodiments of a method of treating a stent may include contacting a polymeric surface of a stent with a treatment fluid. The treatment fluid may include a solvent for the surface polymer. Therefore, the treatment fluid is capable of dissolving at least a portion of the surface polymer.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. A second fluid can act as a non-solvent for the impurity. "Non-solvent" is defined as a substance incapable of dissolving the other substance. The non-solvent should be capable of dissolving only less than 0.1 mg of the polymer in 1 ml of the non-solvent at ambient temperature and ambient pressure, and more narrowly only less than 0.05 mg in 1 ml at ambient temperature and ambient pressure.

Contacting the polymeric surface of the stent with the treatment fluid may be performed by, for example, immersing the stent in the treatment fluid. Additionally, the stent may be sprayed with treatment fluid.

In an embodiment, the treatment fluid can be a pure solvent for the surface polymer or a combination of one or more pure solvents for the surface polymer. In another embodiment, the treatment fluid can be a combination of solvent(s) and non-solvent(s) for the surface polymer such that the solvent(s) and non-solvent(s) are miscible. In one embodiment, the treatment fluid is free (100%) from any polymeric materials, active agents, or drugs.

For example, a treatment fluid for a poly(L-lactide) (PLLA) stent can include chloroform, which is a solvent for PLLA. Thus, a treatment fluid can include a mixture of chloroform and another solvent for PLLA; a mixture of chloroform and a non-solvent for PLLA; or a mixture of chloroform, another solvent for PLLA, and a non-solvent for PLLA. For example, a treatment fluid can include, but is not limited to, a chloroform/isopropyl alcohol (IPA) solution, a chloroform/methyl alcohol solution, or a chloroform/ethyl alcohol solution.

Furthermore, the solvent in the treatment fluid may be allowed to modify at least a portion of the polymeric surface by dissolving at least a portion of the surface polymer. The solvent may be allowed to dissolve surface polymer such that sharp edges of the struts are rounded to a desired degree and to reduce and/or remove all or a substantial portion of undesirable features or imperfections from the surface. The portion of the surface polymer dissolved may correspond to at least a portion of a surface imperfection and/or a sharp edge of a strut. Additionally, the treatment fluid may remove some or all of the low molecular weight material caused by exposure to the laser during laser machining from the surface. Also, the heat affected zone caused by laser cutting can be removed to improve mechanical properties.

In addition, the degree of modification of the polymeric surface depends at least in part on the contact time of the treatment fluid with the polymeric surface. For example, a stent can be sprayed a selected period of time to obtain a desired degree of modification of a polymeric surface. Also, spraying the treatment fluid tends to result in a polymer solution on the polymer surface that includes the surface polymer dissolved in the treatment fluid. The polymer solution may tend to flow at or near the surface resulting in modification of the polymeric surface. The treatment fluid may be allowed to remain on the surface of the stent a period of time to modify the surface after spraying is completed.

In some embodiments, the stent can be sprayed with a conventional spray apparatus, or applied by other metering devices. Fluid can be sprayed in the form of atomized droplets or in the form of a concentrated fluid stream. For instance, the stent can be sprayed for one to ten spray cycles (i.e., back and forth passes along the length of the stent) using a spray apparatus to deposit about 1 ml to about 500 ml, more narrowly 5 ml to about 20 ml, of the treatment fluid onto the stent. The spray process can take place in a vacuum chamber at a reduced pressure (e.g., less than 300 mm Hg) in order to raise the treatment fluid concentration in the vapor phase.

In some embodiments, the polymeric surface of a stent can be selectively treated with the treated by selectively contacting a region of the polymeric surface of a stent. In one embodiment, a fluid stream from a spray apparatus can be directed selectively at regions such as surfaces that have been laser cut or regions having imperfections.

Additionally, after a desired degree of modification of the surface of the stent, the method of treatment may further include contacting the polymeric surface with a second fluid miscible with the solvent to remove all or a majority of the treatment fluid from the surface of the stent. In one embodiment, the second fluid can be a non-solvent for the surface polymer. Thus, the second fluid can remove treatment fluid without further modification of the polymeric surface. The second fluid can also remove all or a majority of dissolved surface polymer from the polymeric surface.

In one embodiment, the polymeric surface is contacted with a second fluid by immersing the stent in the second fluid. Alternatively, the second fluid can be sprayed or deposited on the surface of the stent to rinse all or a majority of the treatment fluid and any dissolved surface polymer from the surface of the stent. For example, a second fluid for removal of a treatment fluid that includes chloroform for a PLLA stent can include IPA or methyl alcohol.

In addition, the treatment method may further include removing all or a majority of the second fluid from the polymer surface of the stent. For example, a gas such as air can be blown on the stent to cause the second fluid to evaporate. Also, the stent can be baked in an oven, such as a vacuum oven, to remove the second fluid from the stent.

It is desirable to maximize the surface area of the stent that is treated. Therefore the support for the stent may be selected such that contact between the support and the stent is minimized. In one embodiment, the stent may be positioned on a tubular support such as a mandrel. Typically, a mandrel is configured to rotate about its cylindrical axis. A stent such as that depicted in FIG. 1 may be positioned about the axis of the mandrel. A mandrel that is inserted into the bore of a stent can, however, mask the inner surface of the stent so as to prevent proper treatment of the inner surface of the stent. Accordingly, it is preferable to use a support assembly that allows for proper access to the inner or luminal surface of the stent and not just the outer or abluminal surface of the stent. The mandrel can include, for example, a first element that supports a first end of the stent and a second element that supports a second end of the stent. Examples in the patent literature teaching these types of mandrels include U.S. Pat. No. 6,527,863 to Pacetti et al. and U.S. Pat. No. 6,605,154 to Villareal. The mandrel, accordingly does not make contact with a luminal surface of the stent and allows for proper modification of all surfaces.

Further embodiments of a method for treating a polymeric surface of a stent may include contacting the polymeric surface of the stent with a gas stream. The gas stream can include a solvent for the surface polymer that is capable of dissolving the surface polymer. The solvent in the gas may be allowed to modify at least a portion of the polymeric surface by dissolving at least a portion of the surface polymer.

In one embodiment, gas stream treatment can be performed in conjunction with island removal from a laser cut stent. "Islands" refer to pieces or portions of polymeric tubing material that are intended to be part of a stent pattern that remain attached to stent struts after laser cutting. The pieces or portions may have a relatively weak physical attachment to a strut or may be wedged between struts with not physical attachment to the struts. Due to the weak attachment, islands can be removed by blowing gas stream at or near the islands.

In one embodiment, the gas stream can be a solvent vapor. The solvent vapor can be a pure solvent for the surface polymer or a combination of one or more pure solvents for the surface polymer. In another embodiment, the solvent vapor can be a combination of solvent(s) and non-solvent(s) for the surface polymer. For example, for a treatment of a PLLA stent, chloroform and the chloroform mixtures described above may be used as a solvent vapor.

A stream of solvent vapor may be generated in a variety of ways that are known in the art. For example, a solvent vapor may be created in a closed container by heating the solvent above its boiling point. The solvent vapor may then be transported from the container from a tube or hose at an increased pressure for treatment.

In another embodiment, the gas stream can be a mixture of a solvent and an inorganic gas such as air, argon, oxygen, nitrogen, carbon dioxide, etc. The relative composition of the solvent in the gas stream can be varied to control the degree of modification of a polymeric surface. For example, the solvent can be greater than 10%, 30%, 50%, 70%, 80%, or 90% volume percent of the gas.

The gas mixture can be prepared by passing a gas such as air, argon, oxygen, nitrogen, carbon dioxide, etc. through a liquid solvent. For example, the gas can be bubble up through a container of liquid solvent. The gas mixture exiting the liquid is a mixture of the gas and the solvent. The volume fraction of solvent in the gas mixture can be controlled by varying the temperature of the solvent or gas passed into the liquid solvent. Increasing the temperature increases the fraction of solvent in the gas mixture. Additionally, the pressure above the solvent can be varied to modify the fraction of solvent in the gas mixture. Decreasing the pressure will increase the fraction of solvent in the gas mixture.

Another way of generating a gas mixture of solvent and a gas may include spraying a liquid solvent with a spray apparatus, as described above. A nozzle can be selected that generates atomized droplets that evaporate before or after exiting the nozzle, creating a solvent-air gas stream. Additionally, the treatment process can be performed in a closed chamber at a reduced pressure to facilitate evaporation of the atomized droplets.

In one embodiment, a nozzle can direct the gas stream at the surface of the stent. The stent can be mounted on a support and the nozzle can be positioned adjacent to into a proximal or distal end of the stent. For example, FIG. 6 depicts a stent 600 with a nozzle 610 positioned above stent 600 and a nozzle 620 directed into a proximal end of stent 600. During treatment, the nozzle can be translated with respect to the stent and/or the stent can be rotated and translated with respect to the nozzle.

In an embodiment, the gas stream can be heated to reduce condensation of solvent on the stent. The gas stream can be heated to a temperature above its boiling point at the treatment pressure. Treatment of the stent with the gas stream can be performed in a closed chamber to control the treatment pressure. Treatment can be performed at a reduced pressure in order to reduce condensation of the solvent vapor.

In some embodiments, the polymeric surface of a stent can be selectively treated with the gas stream by selectively contacting a region of the polymeric surface of a stent. In one embodiment, the gas stream can be directed selectively at regions such as surfaces that have been laser cut or regions having imperfections. Selective modification can reduce solvent exposure to substrate or a coating where treatment is not desired. Reducing exposure can be desirable since a solvent can have negative effects on the mechanical properties of treated regions.

Figure 7A:
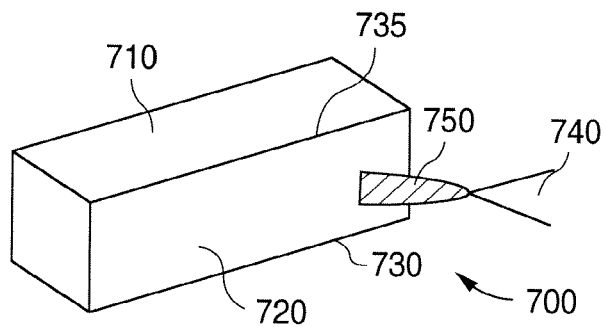
FIGS. 7A and 7B depict selective modification of surface imperfections on a stent.

FIG. 7A depicts a portion 700 of a strut showing an abluminal surface 710 and sidewall surface 720. Portion 700 has sharp edges 730 and 735 at the edge of sidewall surfaces 720. A nozzle 740 can selectively treat sidewall surfaces 720 and sharp edges 730 and 735 with a gas stream 750.

Also, selective treatment can be advantageous since some regions require more treatment than others. For example, some regions may require particularly aggressive treatment. An aggressive treatment of a polymeric surface without selective modification can remove a substantial amount of surface polymer than requires little or no treatment. An aggressive treatment may include exposure to a treatment solvent with a stronger solvent, a higher concentration of solvent, and/or exposure to solvent for a longer period of time.

Figure 7B:
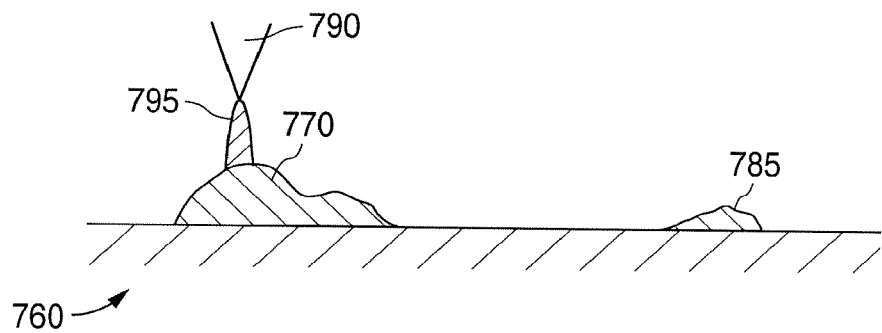

Referring to FIG. 7B as an example, a portion of a strut 760 has a protrusion 770 that is substantially larger than a protrusion 785. A nozzle 790 can selectively treat protrusion 770 with a gas stream 795.

A system for selectively treating a stent with a gas stream from a nozzle can be developed from a controlled deposition system that applies various substances only to certain targeted portions of an implantable medical device such as a stent. A representative example of such a system, and a method of using the same, is described in U.S. Pat. No. 6,395,326 to Castro et al. A laser machining system for cutting stent patterns can also be adapted to selective treatment of a stent with a gas stream. Systems for laser machining stents have been described in numerous patents including U.S. Pat. Nos. 6,521,865 and 6,131,266.

A selective gas treatment system can be capable of directing a gas stream in or on a stent having a complex geometry, and otherwise directing the gas stream so that the treatment is limited to particular portions of the stent. The system can have a nozzle and a holder that supports the stent. The nozzle and/or holder can be capable of moving in very small intervals, for example, less than about 0.001 inch. Furthermore, the nozzle and/or holder can be capable of moving in the x-, y-, or z-direction, and be capable of rotating about a single point.

The holder supporting the stent and/or the nozzle can be moved in a predetermined path by a machine-controlled system. The nozzle can selectively treat portions of the pattern of the stent as the stent and/or nozzle are moved relative to one another. CNC equipment manufactured and sold by Anorad Corporation may be used for positioning a stent and/or nozzle.

Additional embodiments of treating a polymeric surface of a stent include contacting a polymeric surface of a stent with a treatment fluid mixed with particles. The treatment fluid can include a solvent for the surface polymer that is capable of dissolving the surface polymer. The solvent in the fluid and the particles may be allowed to modify at least a portion of the polymeric surface. As in the embodiments described above, the solvent can modify the surface by dissolving at least a portion of the surface polymer. The particles can modify the polymeric surface by abrading the polymeric surface.

Other embodiments of treating a polymeric surface of a stent include contacting a polymeric surface of a stent with particles mixed with a gas. In one embodiment the gas may be a nonsolvent or inert to the surface polymer such as air, nitrogen, oxygen, argon, etc. In another embodiment, the gas may include a solvent for the surface polymer.

In some embodiments, the particles can have a characteristic length, such as a diameter, between about 0.001 microns and about 10 microns. The particles can be composed of materials including, but not limited to, silicon, silicon carbide, aluminum oxide, and bicarbonate of soda.

The degree of abrasion can be controlled or modified by the concentration of particles in the treatment fluid. The concentration of microbeads in the treatment fluid can be less than 50 wt %, 40 wt %, 30 wt %, 20 wt %, or more narrowly, less than 10 wt %.

As above, the treatment fluid can be a pure solvent for the surface polymer or a combination of one or more pure solvents for the surface polymer. Alternatively, the treatment fluid can be a combination of solvent(s) and non-solvent(s) for the surface polymer such that the solvent(s) and non-solvents are miscible. Additionally, the method may further include contacting the polymeric surface with a second fluid miscible with the solvent to remove all or a majority of the first fluid and the particles from the polymeric surface. The second fluid may be a non-solvent for the surface polymer. The stent can be immersed in, sprayed, or rinsed with the second fluid.

Various embodiments may be contemplated for causing abrasion of the polymeric surface by the particles in the treatment fluid. Generally, it is necessary to induce movement or flow of treatment fluid around the stent so that abrasion of the polymeric surface by the particles can occur.

Figure 8A:
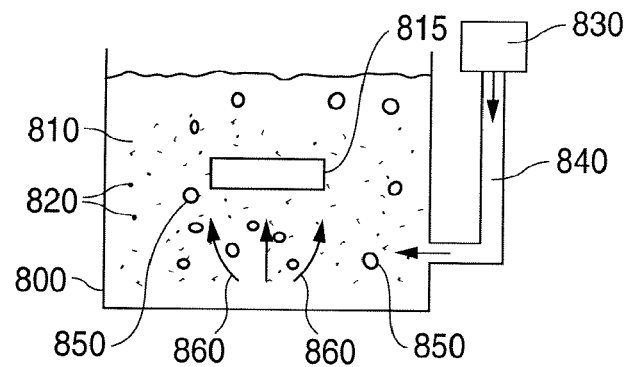
FIG. 8A-B depicts treatment of a stent surface with an agitated mixture of fluid and particles.

One embodiment can include immersing the stent in bath of liquid treatment fluid mixed with particles in which agitation of the bath causes abrasion by the particles of the polymeric surface. Such an embodiment is similar to a fluidized bed. For example, FIG. 8A depicts a container 800 including a treatment fluid 810 and particles 820 mixed or suspended in treatment fluid 810. A stent 815 supported or suspended by a holder (not shown) in container 800. Container 800 is in fluid communication with a gas source 830 through a tube 840. Fluid source 830, which can be a pump or blower, injects or forces air or some other conveniently available gas through tube 840 into container 800 to form bubbles 850 that pass through treatment fluid 810. The upward movement of bubbles 850 induce movement and flow of treatment fluid 810 and particles 820, as shown by arrows 860. Treatment fluid 810 dissolves at least a portion of the surface polymer of stent 815 and moving particles 820 abrade the surface polymer of stent 815.

Figure 8B:
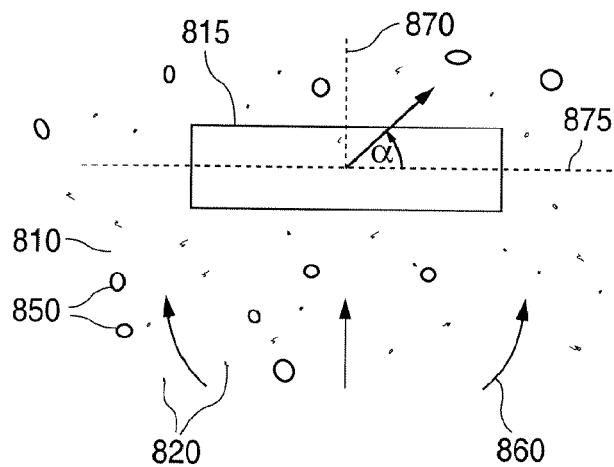

Additionally, stent 815 can be rotated to more uniformly abrade its surface. FIG. 8B depicts a close-up view of stent 815. Stent 815 can be rotated about an axis 870 by an angle α. For example, rotating stent 815 by an angle α of 90° or −90° results in an end of the stent facing the upward movement of particles. Rotation can be performed continuously or discretely. For example, stent 815 can remain at an angle α' for a period of time, rotated to a new angle α", and remain fixed for another period of time. Additionally, stent 815 can be rotated, continuously or discretely about its longitudinal axis 875.

Figure 9A:
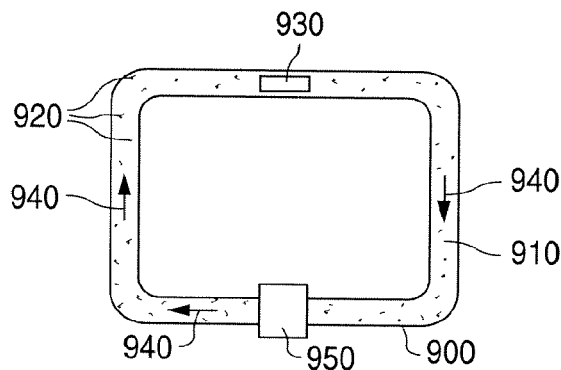
FIG. 9A-B depicts treatment of a stent surface in a tube.

Another embodiment of abrading the polymeric surface of a stent can include flowing a treatment fluid mixed with particles past a stent disposed within a tube. FIG. 9A depicts a tube 900 including a treatment fluid 910 with particles 920 mixed or suspended in treatment fluid 910. Treatment fluid 910 can be a liquid including a solvent for the surface polymer. Also, treatment fluid 910 can be a solvent vapor or a gas mixture including a solvent for the surface polymer and a gas that is a nonsolvent for the surface polymer. Alternatively, rather than treatment fluid 910, particles 920 can be mixed with a gas that is a nonsolvent for the surface polymer such as air, nitrogen, oxygen, argon, etc. In this alternative, treatment of the surface polymer is entirely due to abrading by the particles. A stent 930 is suspended or secured by a holder (not shown) within tube 900 with the axis of the stent parallel to the axis of the tube. Tube 900 is connected to a reversible pump 950 that can induce a flow of treatment fluid 910 and particles 920, as shown by arrows 940. Treatment fluid 910 dissolves at least a portion of the surface polymer of stent 930 and flowing particles 920 abrade the surface polymer of stent 930.

Figure 9B:
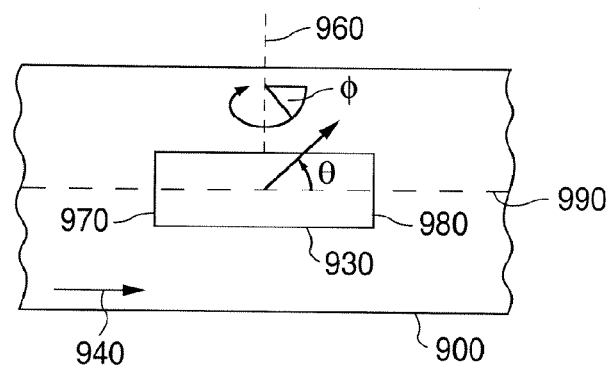

The flowing particles 920 tend to abrade to a greater degree surfaces of the stent facing the direction of flow 940. To abrade surfaces facing way from the flow, the direction of flow can be reversed. Alternatively, stent 930 can be rotated to more uniformly abrade the surface of stent 930. FIG. 9B depicts a close-up view of stent 930 disposed in tube 900. Stent 930 can be rotated about axis 960 by an angle ϕ. For example, rotating stent 960 by an angle ϕ of 180° results in reversal of proximal end 970 and distal end 980, such that distal end 680 faces the direction of flow as shown by arrow 940. Rotation can be performed continuously or discretely. For example, stent 930 can remain at an angle ϕ' for a period of time, rotated to a new angle ϕ", and remain fixed for another period of time. Additionally, stent 930 can be rotated, continuously or discretely, so that its axis 990 is at an angle θ with respect to the direction of flow 940, which is the same as the axis of tube 900. After treatment of the stent is completed, the mixture of treatment fluid and particles can be replaced with a non-solvent. The flow of the non-solvent can remove all or substantially all of the treatment fluid from the stent surface.

Furthermore, the flow rate of treatment fluid 910 and particles 920 can affect the degree of surface modification. Generally, the faster the flow rate, the more and faster is the degree of abrasion. Additionally, the degree and uniformity of abrasion may depend upon whether the flow through a tube is laminar or turbulent. Laminar flow is characterized by smooth, constant fluid motion, while turbulent flow, on the other hand, producing random eddies, vortices and other flow fluctuations. The transition between laminar and turbulent flow is often indicated by a critical Reynolds number ($Re_{crit}$), which depends on the exact flow configuration and must be determined experimentally. The Reynolds number is given by:

$$Re = \rho v_s L/\mu$$

or $$Re = \rho v_s L/\nu$$

where:

$v_s$—mean fluid velocity,

L—characteristic length (equal to diameter 2r if a cross-section is circular),

μ—(absolute) dynamic fluid viscosity,

ν—kinematic fluid viscosity: $\nu=\mu/\rho$,

ρ—fluid density.

Within a certain range around $Re_{crit}$ there is a region of gradual transition where the flow is neither fully laminar nor fully turbulent. For example, within circular pipes or tubes the critical Reynolds number is generally accepted to be 2300, where the Reynolds number is based on the tube diameter and the mean velocity within the pipe. The random eddies, vortices and other flow fluctuations of turbulent flow may lead to a higher degree and more uniform abrasion of a polymeric surface.

Figure 10:
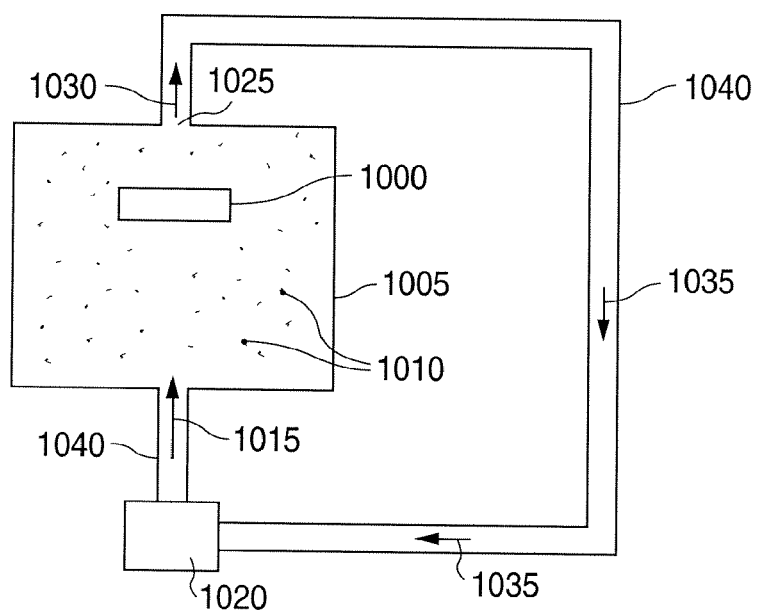
FIG. 10 depicts treatment of a stent surface in a container with gas and particles.

An additional embodiment of treating the polymeric surface of a stent depicted in FIG. 10 includes disposing a stent 1000 in a container 1005 containing particles 1010. The embodiment of FIG. 10 is also similar to a fluidized bed. A gas is blown into container 1010, as shown by an arrow 1015, by a pump or a blower 1020. The gas induces movement of particles 1010 which abrade the polymeric surface of stent 1000. The gas can be a solvent vapor or a gas mixture including a solvent for the surface polymer and a nonsolvent for the surface polymer. Alternatively, the gas can be a nonsolvent for the surface polymer such as air, nitrogen, oxygen, argon, etc. In this alternative, treatment of the surface polymer is entirely due to abrading by the particles.

Gas exits container 1010 at air outlet 1025, as shown by an arrow 1030. Gas can be recirculated to pump or blower 1020 through tube 1040, as shown by arrows 1035. Air outlet 1025 can have a filter to prevent particles from entering tube 1040. Alternatively, the gas may not be recirculated.

Additionally, some embodiments of the method treating a polymeric surface of a stent may include removing at least some impurities at or near the surface of the stent prior to contacting the surface of the stent with treatment fluid. Impurities may include particles and/or contaminants that may reduce the effectiveness of the treatment process. One method of removing impurities may include ultrasonic cleaning In an ultrasonic cleaning process a stent may be immersed in a bath of a suitable fluid. Representative examples of suitable fluids may include alcohols such as isopropyl alcohol, water, or any other fluid that is inert to the polymer during the time frame of the cleaning process. Removal of impurities may be achieved by subjecting the bath to ultrasonic cavitation. Cavitation refers to the formation of partial vacuums in a liquid. Standard ultrasonic baths operate at a frequency of about 40 kHz. The stent may be subjected to the ultrasonic bath for about one minute to about ten minutes, or more narrowly from about one to about three minutes. Ultrasonic cleaning may be followed by rinsing and drying of the stent. Rinsing may be performed with the cleaning solution. The stent may be air dried, or baked in an oven.

Representative examples of solvents that may be used in accordance with the present invention include, but are not limited to, acetone, chloroform, hexafluoroisopropanol, 1,4-dioxane, tetrahydrofuran (THF), dichloromethane acetonitrile, dimethyl sulfoxide (DMSO), and dimethylformamide (DMF), cyclohexane, toluene, xylene, acetone, ethyl acetate.

Polymers for use in fabricating a substrate of a stent or a coating for a stent can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an stent include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A non-polymer substrate of the stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa.. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLE

Figure 11:
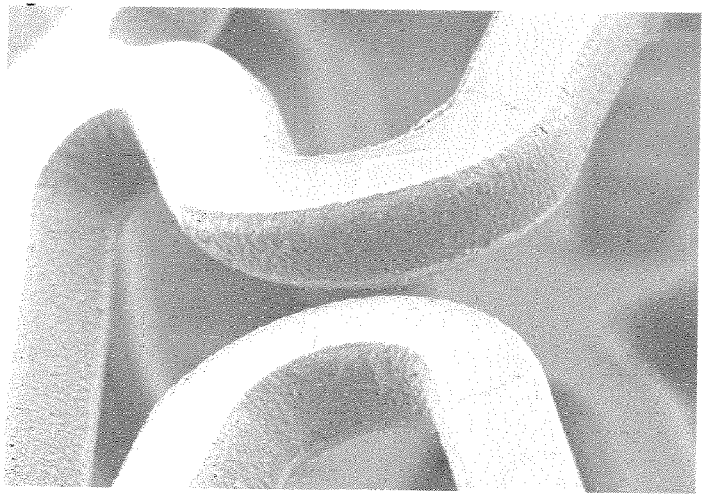
FIGS. 11 and 12 are photographs of a poly(L-lactide) stent treated with chloroform according to methods of the present invention.
Figure 12:
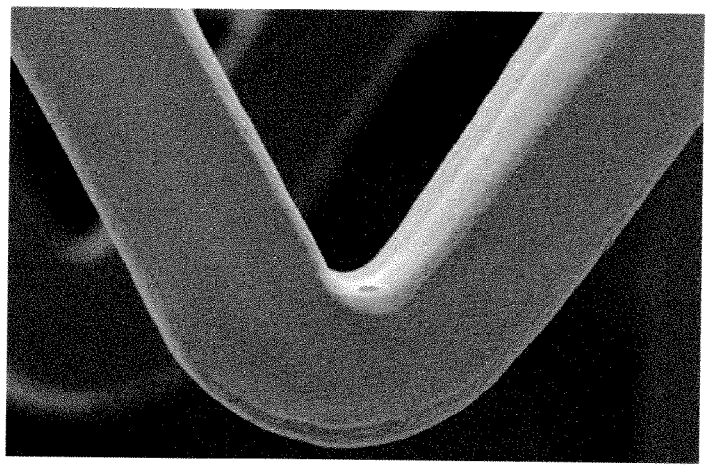

FIGS. 11 and 12 are photographs of a poly(L-lactide) stent treated with chloroform according to methods of the present invention. As shown in both FIGS. 10 and 11, the edges of the struts of the stent are smooth and rounded.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method for forming a stent, comprising:
providing a tube formed from a polymer material;
laser cutting the polymer tube to form a laser cut polymer tube including first and second struts, wherein the laser cutting forms an undesired portion on the first and second struts, wherein the undesired portion is one or more of a lower molecular weight material disposed over the first and second struts, cracks, sharp edges and imperfections on or adjacent to the first and second struts; and
applying a gas stream to the laser cut tube to remove substantially the entire undesired portion from the laser cut tube.

2. The method for forming a stent of claim 1, wherein the applying step further includes directing a nozzle towards only the undesired portion, the nozzle dispensing the gas stream.

3. The method for forming a stent of claim 2, wherein an abrasive comprising particles is dispersed within the gas stream.

4. The method for forming a stent of claim 1, wherein a bore axis of the laser cut tube is arranged at an acute angle to a free stream fluid flow direction of the gas stream.

5. The method of claim 1, wherein the gas stream contacts the polymeric surface with a nozzle directing the gas stream at the undesired portion.

6. The method of claim 1, wherein the gas stream comprises chloroform and the surface polymer comprises poly(L-lactide).

7. The method of claim 1, wherein the surface polymer is a biostable polymer, biodegradable polymer, or a combination thereof.

8. A method for forming a stent, comprising:
providing a tube formed from a polymer material;
laser cutting the polymer tube to form a laser cut polymer tube including first and second struts, wherein the laser cutting forms an undesired portion on the first and second struts, wherein the undesired portion is one or more of a lower molecular weight material disposed over the first and second struts, cracks, sharp edges and imperfections on or adjacent to the first and second struts;
placing the laser cut tube in a second tube, and
removing the undesired portion by causing a solvent and/or abrasive to flow through the second tube while the laser cut tube is in the second tube.

9. The method of claim 8, wherein the solvent and/or abrasive comprises a fluid.

10. The method of claim 8, wherein the removing the undesired portion includes causing the solvent and/or abrasive to flow through the second tube in a first direction to remove substantially a first part of the undesired portion from the laser cut tube, then causing the solvent and/or abrasive to flow through the second tube in a second direction to remove substantially a second part of the undesired portion from the laser cut tube.

11. The method of claim 10, wherein the second tube is connected to a reversible pump.

12. The method of claim 8, wherein the removing the undesired portion includes causing the solvent and/or abrasive to flow through the second tube while the laser cut tube is orientated in a first direction, changing the laser cut tube orientation from the first direction to a second direction, and causing the solvent and/or abrasive to flow through the second tube while the laser cut tube is orientated in the second direction.

13. The method of claim 8, wherein the laser cut tube is rotated 180 degrees when its orientation is changed from the first direction to the second direction.

14. The method of claim 8, wherein the laser cut tube is rotated about its longitudinal axis while the solvent and/or abrasive flows through the second tube.

15. The method of claim 8, wherein while the laser cut tube is being orientated from the first direction to the second direction the solvent and/or abrasive flows through the second tube.

16. The method of claim 15, wherein the laser cut tube rotates continuously from, or between discrete orientations when its orientation is changed from the first direction to the second direction while the solvent and/or abrasive flows through the second tube.

* * * * *